(12) United States Patent
Grether et al.

(10) Patent No.: US 8,455,501 B2
(45) Date of Patent: Jun. 4, 2013

(54) N-(5-CYCLOALKYL)-PYRIDIN-3-YL CARBOXAMIDES

(75) Inventors: Uwe Grether, Efringen-Kirchen (DE); Stephan Roever, Inzlingen (DE)

(73) Assignee: Hoffmann-La Roche Inc, Nutley, NJ (US)

( * ) Notice: Subject to any disclaimer, the term of this patent is extended or adjusted under 35 U.S.C. 154(b) by 0 days.

(21) Appl. No.: 13/607,859

(22) Filed: Sep. 10, 2012

(65) Prior Publication Data

US 2013/0065911 A1  Mar. 14, 2013

(30) Foreign Application Priority Data

Sep. 12, 2011 (EP) .................................... 11180930

(51) Int. Cl.
| | |
|---|---|
| C07D 401/12 | (2006.01) |
| C07D 413/12 | (2006.01) |
| C07D 213/75 | (2006.01) |
| A61K 31/4439 | (2006.01) |
| A61K 31/444 | (2006.01) |
| A61K 31/4418 | (2006.01) |
| A61K 31/506 | (2006.01) |
| A61P 3/06 | (2006.01) |

(52) U.S. Cl.
USPC .......... 514/256; 514/332; 514/335; 514/340; 514/341; 514/345; 514/349; 514/352; 546/261; 546/262; 546/271.4; 546/275.4; 546/292; 544/333

(58) Field of Classification Search
None
See application file for complete search history.

(56) References Cited

U.S. PATENT DOCUMENTS 6,034,272 A  3/2000  Commons et al.

FOREIGN PATENT DOCUMENTS

| WO | 2006/106054 | 10/2006 |
|---|---|---|
| WO | 2008/040651 | 4/2008 |

OTHER PUBLICATIONS

Shinkai, H., "Mini Reviews in Medicinal Chemistry" 2:271-273 ( 2002).
(International Search Report PCT/EP2012/067470 Oct. 10, 2012).

*Primary Examiner* — Sreeni Padmanabhan
*Assistant Examiner* — Irina Neagu

(57) ABSTRACT

The present invention relates to compounds of the formula

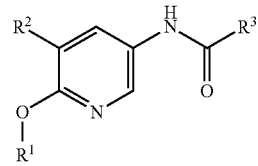

I wherein $R^1$ to $R^3$ are defined in the description, and to pharmaceutically acceptable salts thereof, their manufacture, pharmaceutical compositions containing them and their use as medicaments for the treatment and/or prophylaxis of diseases which can be treated with HDL-cholesterol raising agents, such as particularly dyslipidemia, atherosclerosis and cardiovascular diseases.

11 Claims, No Drawings

N-(5-CYCLOALKYL)-PYRIDIN-3-YL CARBOXAMIDES

PRIORITY TO RELATED APPLICATION(S)

This application claims the benefit of European Patent Application No. 11180930.7, filed Sep. 12, 2011, which is hereby incorporated by reference in its entirety.

FIELD OF THE INVENTION

The present invention is concerned with N-(5-cycloalkyl- or 5-heterocyclyl)-pyridin-3-yl carboxamides being HDL-cholesterol raising agents, their manufacture, pharmaceutical compositions containing them and their use as therapeutically active substances.

The compounds of the invention are HDL-cholesterol raising agents and can therefore be used in the therapeutic and/or prophylactic treatment of diseases and disorders such as dyslipidemia, atherosclerosis and cardiovascular diseases.

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non-esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (10-12%). As a result, there is a significant unmet medical need for a well tolerated agent which can significantly elevate plasma HDL levels.

Thus, HDL-cholesterol raising agents can be useful as medicaments for the treatment and/or prophylaxis of atherosclerosis, peripheral vascular disease, dyslipidemia, hyper-beta-lipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, improvement of glycemic control, obesity or endotoxemia.

In addition, HDL-cholesterol raising agents may be used in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesteryl ester transfer protein (CETP) inhibitor, a cholesterol absorption inhibitor, a cholesterol synthesis inhibitor, a fibrate, niacin, preparations containing niacin or other HM74a agonists, an ion-exchange resin, an antioxidant, an ACAT inhibitor or a bile acid sequestrant.

Object of the present invention is therefore to provide compounds that are potent HDL-cholesterol raising agents. It has been found that the compounds of formula I of the present invention are very useful for the treatment and/or prophylaxis of diseases and disorders which can be treated with HDL-cholesterol raising agents, i.e. the compounds of formula I are especially useful for the treatment and/or prevention of dyslipidemia, atherosclerosis and cardiovascular diseases. Object of the present invention is also to provide compounds which are, at therapeutically active concentrations that increase HDL-concentrations, not interacting with the CB1 receptor. This is because CB1 receptor ligands may compromise the therapeutic utility of HDL-cholesterol raising agents, as both agonists and antagonists of the CB1 receptor have the potential to lead to side effects.

SUMMARY OF THE INVENTION

The present invention relates to compounds of formula (I)

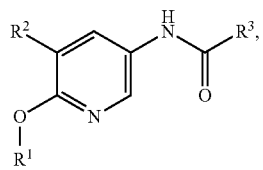

wherein
R$^1$ is selected from the group consisting of C$_{1-7}$-alkyl,
  C$_{3-7}$-cycloalkyl,
  C$_{3-7}$-cycloalkyl-C$_{1-7}$-alkyl,
  hydroxy-C$_{1-7}$-alkyl,
  C$_{1-7}$-alkoxy-C$_{1-7}$-alkyl, and
  halogen-C$_{1-7}$-alkyl;
R$^2$ is selected from the group consisting of
  C$_{3-7}$-cycloalkyl,
  C$_{4-7}$-cycloalkenyl, and
  heterocyclyl, said heterocyclyl having 3 to 7 ring atoms, comprising one, two or three heteroatoms selected from N, O and S and being saturated or partly unsaturated; and
R$^3$ is selected from the group consisting of
  phenyl, wherein phenyl is unsubstituted or substituted by one or two groups selected from the group consisting of C$_{1-7}$-alkyl, hydroxy, C$_{1-7}$-alkoxy, cyano, C$_{3-7}$-cycloalkyl, C$_{3-7}$-cycloalkyl-C$_{1-7}$-alkyl, halogen and halogen-C$_{1-7}$-alkyl, and
  heteroaryl, wherein heteroaryl is unsubstituted or substituted by one or two groups selected from the group consisting of C$_{1-7}$-alkyl, hydroxy, C$_{1-7}$-alkoxy, cyano, C$_{3-7}$-cycloalkyl, C$_{3-7}$-cycloalkyl-C$_{1-7}$-alkyl, halogen and halogen-C$_{1-7}$-alkyl;
and pharmaceutically acceptable salts thereof.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, particularly of one to four carbon atom(s).

The term "alkyl", alone or in combination with other groups, refers to a branched or straight-chain monovalent saturated aliphatic hydrocarbon radical of one to twenty carbon atoms, particularly one to sixteen carbon atoms, more particularly one to ten carbon atoms.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular ethyl, propyl, isopropyl and tert-butyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, in particular methoxy.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups are e.g. —$CH_2$—O—$CH_3$, —$CH_2$—$CH_2$—O—$CH_3$, —$CH_2$—O—$CH_2$—$CH_3$ and the groups specifically exemplified herein. More particularly, lower alkoxyalkyl is methoxyethyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl, more particularly cyclopropyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. Among the lower cycloalkylalkyl groups of particular interest resides cyclopropylmethyl.

The term "halogen" refers to fluoro, chloro, bromo and iodo, with fluoro, chloro and bromo being of particular interest. More particularly, halogen refers to fluoro and chloro.

The term "lower halogenalkyl" or "halogen-$C_{1-7}$-alkyl" refers to lower alkyl groups which are mono- or multiply substituted with halogen, in particular with fluoro or chloro, most particularly with fluoro. Examples of lower halogenalkyl groups are e.g. —$CF_3$, —$CHF_2$, —$CH_2Cl$, —$CH_2CF_3$, —$CH(CF_3)_2$, —$CF_2$—$CF_3$, —$CH_2$—$CH_2$—$CF_3$, —$CH(CH_3)$—$CF_3$ and the groups specifically exemplified herein. Of particular interest are the groups trifluoromethyl (—$CF_3$) and 2,2,2-trifluoroethyl (—$CH_2CF_3$).

The term "cyano" means to group —CN.

The term "heterocyclyl" refers to a saturated or partly unsaturated 3-, 4-, 5-, 6- or 7-membered ring which can comprise one, two or three heteroatoms selected from N, O and S. Examples of heterocyclyl rings include piperidinyl, piperazinyl, azetidinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, oxiranyl, thiadiazolylidinyl, oxetanyl, dioxolanyl, dihydrofuranyl, tetrahydrofuranyl, dihydropyranyl, tetrahydropyranyl, and thiomorpholinyl. Of particular interest is the dihydropyranyl group.

The term "heteroaryl" refers to an aromatic 5- or 6-membered ring which can comprise one, two or three atoms selected from N, O and S. Examples of heteroaryl groups are e.g. furanyl, pyridyl, pyrazinyl, pyrimidinyl, pyridazinyl, thienyl, isoxazolyl, thiazolyl, isothiazolyl, thiadiazolyl, oxazolyl, imidazolyl, pyrazolyl, triazolyl, oxadiazolyl, oxatriazolyl, tetrazolyl, pentazolyl, or pyrrolyl. The term "heteroaryl" also includes bicyclic groups comprising two 5- or 6-membered rings, in which one or both rings are aromatic and can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl, and 3,4-dihydro-2H-pyrido[3,2-b][1,4]oxazinyl. Heteroaryl groups of particular interest are of isoxazolyl, pyrazolyl, oxadiazolyl, thiazolyl, pyridyl, pyridazinyl, pyrimidinyl and pyrazinyl.

"Isomeric forms" are all forms of a compound characterized by having an identical molecular formula but that differ in the nature or the sequence of bonding of their atoms or in the arrangement of their atoms in space. Particularly, the isomeric forms differ in the arrangement of their atoms in space and can also be termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

The term "pharmaceutically acceptable salts" refers to those salts which retain the biological effectiveness and properties of the free bases or free acids, and which do not possess any own properties that are undesirable. The salts are formed with inorganic acids such as hydrochloric acid, hydrobromic acid, sulfuric acid, nitric acid, phosphoric acid and the like, particularly hydrochloric acid, and organic acids such as formic acid, acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. Thus, preferred "pharmaceutically acceptable salts" include the acetate, bromide, chloride, formate, fumarate, maleate, mesylate, nitrate, oxalate, phosphate, sulfate, tartrate and tosylate salt of compounds of formula I. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, diethylamine, lysine, arginine, N-ethylpiperidine, piperidine, piperazine and the like. The compound of formula I can also be present in the form of zwitterions or in the form of hydrates. Particularly preferred pharmaceutically acceptable salts of compounds of formula I are the hydrochloride salts.

The present invention relates to compounds of formula (I)

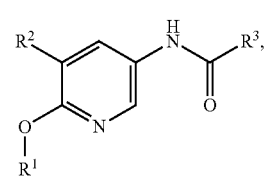

wherein
$R^1$ is selected from the group consisting of $C_{1-7}$-alkyl,
  $C_{3-7}$-cycloalkyl,
  $C_{3-7}$-cycloalkyl-$C_{1-7}$-alkyl,
  hydroxy-$C_{1-7}$-alkyl,
  $C_{1-7}$-alkoxy-$C_{1-7}$-alkyl, and
  halogen-$C_{1-7}$-alkyl;

$R^2$ is selected from the group consisting of
  $C_{3-7}$-cycloalkyl,
  $C_{4-7}$-cycloalkenyl, and
  heterocyclyl, said heterocyclyl having 3 to 7 ring atoms, comprising one, two or three heteroatoms selected from N, O and S and being saturated or partly unsaturated; and
$R^3$ is selected from the group consisting of
  phenyl, wherein phenyl is unsubstituted or substituted by one or two groups selected from the group consisting of $C_{1-7}$-alkyl, hydroxy, $C_{1-7}$-alkoxy, cyano, $C_{3-7}$-cycloalkyl, $C_{3-7}$-cycloalkyl-$C_{1-7}$-alkyl, halogen and halogen-$C_{1-7}$-alkyl, and
  heteroaryl, wherein heteroaryl is unsubstituted or substituted by one or two groups selected from the group consisting of $C_{1-7}$-alkyl, hydroxy, $C_{1-7}$-alkoxy, cyano, $C_{3-7}$-cycloalkyl, $C_{3-7}$-cycloalkyl-$C_{1-7}$-alkyl, halogen and halogen-$C_{1-7}$-alkyl;
and pharmaceutically acceptable salts thereof.

Compounds of formula I according to the present invention are in particular those, wherein $R^1$ is $C_{3-7}$-cycloalkyl-$C_{1-7}$-alkyl or halogen-$C_{1-7}$-alkyl. More particularly, $R^1$ is halogen-$C_{1-7}$-alkyl. Most particularly, $R^1$ is 2,2,2-trifluoroethyl.

Compounds of formula I according to the present invention are furthermore those, wherein $R^2$ is $C_{3-7}$-cycloalkyl or $C_{4-7}$-cycloalkenyl. In particular, $R^2$ is selected from cyclopentyl, cyclohexyl, cyclopenten-1-yl and cyclohexen-1-yl. More particularly, $R^2$ is cyclopentyl or cyclohexyl.

Another group of compounds of formula I according to the present invention are those,
wherein $R^2$ is heterocyclyl, said heterocyclyl having 3 to 7 ring atoms, comprising one, two or three heteroatoms selected from N, O and S and being saturated or partly unsaturated. More particularly, $R^2$ is 3,6-dihydro-2H-pyran-4-yl.

Compounds of formula I according to the present invention are further those, wherein $R^3$ is phenyl, wherein phenyl is unsubstituted or substituted by one or two groups selected from the group consisting of $C_{1-7}$-alkyl, hydroxy, $C_{1-7}$-alkoxy, cyano, $C_{3-7}$-cycloalkyl, $C_{3-7}$-cycloalkyl-$C_{1-7}$-alkyl, halogen and halogen-$C_{1-7}$-alkyl, or
heteroaryl, wherein heteroaryl is unsubstituted or substituted by one or two groups selected from the group consisting of $C_{1-7}$-alkyl, hydroxy, $C_{1-7}$-alkoxy, cyano, $C_{3-7}$-cycloalkyl, $C_{3-7}$-cycloalkyl-$C_{1-7}$-alkyl, halogen and halogen-$C_{1-7}$-alkyl.

In particular, the invention relates to compounds of formula I, wherein $R^3$ is heteroaryl, wherein heteroaryl is unsubstituted or substituted by one or two groups selected from the group consisting of $C_{1-7}$-alkyl, hydroxy, $C_{1-7}$-alkoxy, cyano, $C_{3-7}$-cycloalkyl, $C_{3-7}$-cycloalkyl-$C_{1-7}$-alkyl, halogen and halogen-$C_{1-7}$-alkyl.

Particularly, the heteroaryl group is selected from the group consisting of furanyl, oxazolyl, isoxazolyl, pyrazolyl, oxadiazolyl, thiazolyl, isothiazolyl, thiodiazolyl, pyridyl, pyridazinyl, pyrimidinyl and pyrazinyl, particularly from the group consisting of oxazolyl, pyrazolyl, pyridyl, and pyrimidinyl, said heteroaryl being unsubstituted or substituted by one or two groups selected from the group consisting of $C_{1-7}$-alkyl, hydroxy, $C_{1-7}$-alkoxy, cyano, $C_{3-7}$-cycloalkyl, $C_{3-7}$-cycloalkyl-$C_{1-7}$-alkyl, halogen and halogen-$C_{1-7}$-alkyl. More particularly, the heteroaryl group is selected from pyridyl and pyrimidinyl.

In particular, the invention relates to compounds of formula I, wherein $R^3$ is selected from the group consisting of 5-methyl-oxazol-4-yl, 5-methyl-2H-pyrazol-3-yl, pyridin-2-yl, pyridin-3-yl, 5-methoxy-pyridin-3-yl and pyrimidin-5-yl. More particularly, $R^3$ is selected from pyridin-2-yl, 5-methoxy-pyridin-3-yl and pyrimidin-5-yl.

Another group of compounds of formula I are those, wherein $R^3$ is phenyl, wherein phenyl is unsubstituted or substituted by one or two groups selected from the group consisting of $C_{1-7}$-alkyl, hydroxy, $C_{1-7}$-alkoxy, cyano, $C_{3-7}$-cycloalkyl, $C_{3-7}$-cycloalkyl-$C_{1-7}$-alkyl, halogen and halogen-$C_{1-7}$-alkyl. More particularly, $R^3$ is phenyl.

Particular compounds of formula I of the present invention are the following:
N-[5-cyclopentyl-6-(2,2,2-trifluoro-ethoxy)-pyridin-3-yl]-5-methoxy-nicotinamide,
5-methyl-2H-pyrazole-3-carboxylic acid [5-cyclopentyl-6-(2,2,2-trifluoro-ethoxy)-pyridin-3-yl]-amide,
5-methyl-oxazole-4-carboxylic acid [5-cyclopentyl-6-(2,2,2-trifluoro-ethoxy)-pyridin-3-yl]-amide,
N-[5-cyclopentyl-6-(2,2,2-trifluoro-ethoxy)-pyridin-3-yl]-nicotinamide, pyridine-2-carboxylic acid [5-cyclopentyl-6-(2,2,2-trifluoro-ethoxy)-pyridin-3-yl]-amide,
N-[5-cyclopentyl-6-(2,2,2-trifluoro-ethoxy)-pyridin-3-yl]-benzamide, pyrimidine-5-carboxylic acid [5-cyclopentyl-6-(2,2,2-trifluoro-ethoxy)-pyridin-3-yl]-amide,
N-[5-cyclohexyl-6-(2,2,2-trifluoro-ethoxy)-pyridin-3-yl]-nicotinamide,
5-methyl-2H-pyrazole-3-carboxylic acid [5-cyclohexyl-6-(2,2,2-trifluoro-ethoxy)-pyridin-3-yl]-amide,
5-methyl-oxazole-4-carboxylic acid [5-cyclohexyl-6-(2,2,2-trifluoro-ethoxy)-pyridin-3-yl]-amide,
pyridine-2-carboxylic acid [5-cyclohexyl-6-(2,2,2-trifluoro-ethoxy)-pyridin-3-yl]-amide,
N-[5-cyclohexyl-6-(2,2,2-trifluoro-ethoxy)-pyridin-3-yl]-5-methoxy-nicotinamide,
N-[5-cyclohexyl-6-(2,2,2-trifluoro-ethoxy)-pyridin-3-yl]-benzamide,
or pharmaceutically acceptable salts thereof.

More particularly, compounds of formula I of the present invention are the following:
pyrimidine-5-carboxylic acid [5-cyclopentyl-6-(2,2,2-trifluoro-ethoxy)-pyridin-3-yl]-amide,
pyridine-2-carboxylic acid [5-cyclohexyl-6-(2,2,2-trifluoro-ethoxy)-pyridin-3-yl]-amide,
N-[5-cyclohexyl-6-(2,2,2-trifluoro-ethoxy)-pyridin-3-yl]-5-methoxy-nicotinamide,
or pharmaceutically acceptable salts thereof.

The compounds of formula I can be prepared by a process, which process comprises coupling a compound of formula

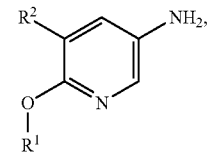

II wherein $R^1$ and $R^2$ are as defined herein before, with a carboxylic acid of the formula

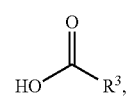

III wherein $R^3$ is as defined herein before, by amide coupling methods known in the art, particularly with the help of an amide coupling agent under basic conditions,
and, if desired, converting the resulting compound of formula I into a pharmaceutically acceptable salt thereof.

Carboxylic acids of formula III may contain functional groups that would interfere with the coupling procedures described for the coupling step (II to I). In this case it is understood that carboxylic acids III need to be suitably protected by methods known in the art before conducting the coupling procedure and compounds need to be deprotected after the coupling step by methods known in the art to deliver compounds of formula I.

Coupling agents for the reaction of compounds of formula II with carboxylic acids of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). In particular, the coupling agent is HATU. Suitable bases include triethylamine, and, particularly, diisopropylethylamine (Hünig's base).

Alternative methods known in the art may commence by preparing the acid chloride from III and coupling with an amine of formula II in the presence of a suitable base.

Following the procedure according to scheme 1, compound AA (3-bromo-2-chloro-5-nitro-pyridine (CAN 5470-17-7) can be used as starting material. AA is commercially available.

Compound AC can be prepared from AA by reaction with a suitably substituted primary or secondary alcohol $R^1$—OH (AB) in the presence of a base, for example potassium hydroxide, in an inert solvent, for example dimethylsulfoxide, at temperatures from room temperature to reflux temperature of the solvent, particularly at room temperature.

Compound AE can be prepared from AC by coupling a suitably substituted alkenyl metal species of formula AD, wherein n is selected from the group consisting of 0, 1, 2 and 3, particularly a cycloalkenylboronic acid ester, in the presence of a suitable catalyst, particularly a palladium catalyst and more particularly palladium(II)chloride-dppf (1,1'-bis(diphenylphosphino)ferrocene) complexes and a base, particularly potassium carbonate in an inert solvent such as dimethylformamide.

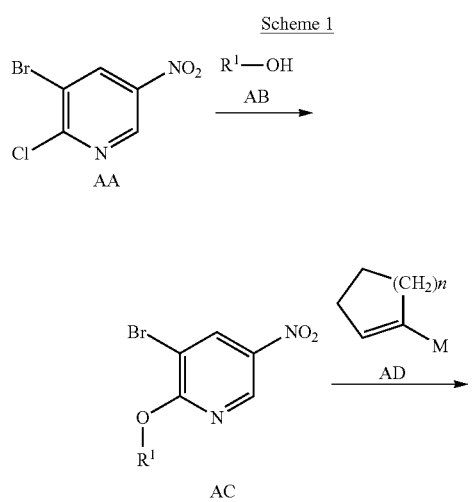

Scheme 1

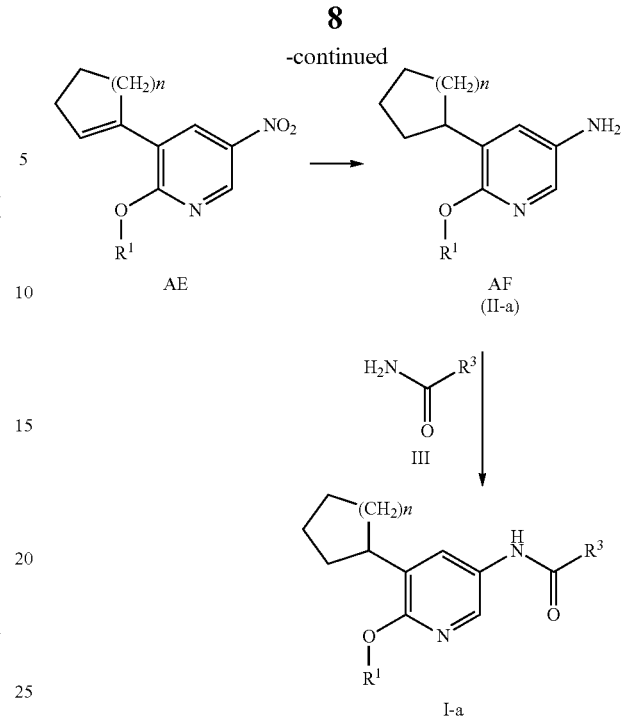

Compound AF (II-a) can be obtained by hydrogenation of compound AE by methods known in the art, for example by hydrogenation with hydrogen gas in the presence of a palladium catalyst, for example palladium on charcoal, in an inert solvent, for example ethyl acetate, at suitable temperatures and pressures, particularly at ambient temperature and pressure.

Compound I-a can be prepared from II-a and the corresponding carboxylic acid of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformations. A convenient method is to use for example TBTU and a base, for example Hünig's base (N-ethyldiisopropylamine) in an inert solvent such as for example dimethylformamide at room temperature.

As described above, the compounds of formula I of the present invention can be used as medicaments for the treatment and/or prophylaxis of diseases which can be treated with HDL-cholesterol raising agents. Examples of such diseases are atherosclerosis, peripheral vascular disease, dyslipidemia, hyperbetalipoproteinemia, hypoalphalipoproteinemia, hyper-cholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia. The use as medicament for the treatment and/or prevention of dyslipidemia, atherosclerosis and cardiovascular diseases is of particular interest.

The invention therefore also relates to pharmaceutical compositions comprising a compound of formula I as defined above and a pharmaceutically acceptable carrier and/or adjuvant. The pharmaceutical compositions are useful in the treatment and/or prophylaxis of diseases which can be treated with HDL-cholesterol raising agents.

Thus, the invention relates to a pharmaceutical composition as defined above for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia.

In another embodiment, the invention relates to a method for the treatment and/or prophylaxis of diseases which can be treated with HDL-cholesterol raising agents, which method comprises administering a therapeutically effective amount of a compound of formula I to a patient in need thereof. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia. A method for the treatment and/or prophylaxis of dyslipidemia, atherosclerosis and cardiovascular diseases is preferred.

The invention also relates to the compounds of formula I for use as medicaments. More specifically, the invention relates to compounds of formula I for use as HDL-cholesterol raising agents. Thus, the invention is concerned with compounds of formula I for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia, in particular for use in the treatment and/or prophylaxis of dyslipidemia, atherosclerosis and cardiovascular diseases.

In addition, the invention relates to the use of compounds of formula I as defined above for the preparation of a medicament for the treatment and/or prophylaxis of diseases can be treated with HDL raising agents. Examples of such diseases are atherosclerosis, peripheral vascular disease, dyslipidemia, hyperbetalipoproteinemia, hypoalphalipoproteinemia, hyper-cholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia. The use of compounds of formula I as defined above for the preparation of medicaments for the treatment and/or prophylaxis of dyslipidemia, atherosclerosis and cardiovascular diseases is of particular interest.

In addition, HDL raising agents of formula I are useful in combination or association with another compound, said compound being selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The invention therefore also relates to pharmaceutical compositions comprising a compound of formula I as defined above in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant, as well as a pharmaceutically acceptable carrier and/or adjuvant.

The invention further relates to compounds of formula I as defined above in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant for use in the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, improvement of glycemic control, obesity or endotoxemia.

The invention also relates to a method for the treatment and/or prophylaxis of diseases which can be treated with HDL-cholesterol raising agents, which method comprises administration of a therapeutically effective amount of a compound according to formula I in combination or association with a therapeutically effective amount of a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

Pharmacological Tests

The following tests were carried out in order to determine the activity of the compounds of formula I and their valuable pharmacological properties.

Detection of upregulation of ABCA1 protein in cells

The ability of compounds of the invention to increase the level of ABCA1 protein is determined in replicate cultures of THP-1 macrophage cells in 96-well microplates. Cells are plated at an initial density of 100,000 cells/well in 100 µl medium and differentiated to adherent macrophages with the addition of PMA (100 nM) for 68 hrs in 10% fetal bovine serum, 3 µl/L of b-mercaptoethanol, RPMI-1640 medium. Then, cells are incubated with RPMI-1640 medium containing 1% FCS, 25 µg/ml acetylated LDL, for 24 hours at 37° C.

Following incubation with acetylated LDL, cells are washed twice with 50 μl PBS and incubated with 100 μl of RPMI-1640 medium containing the compound of interest solubilized in DMSO for an additional 24 hrs. The final DMSO concentration in presence of cells is maintained at 0.5%. ApoA-I binding assay using High Content Image Analysis is initiated by replacing with fresh medium, RPMI without Phenol Red, 0.2% BSA containing AlexaFluor®647 labeled ApoA-I for 2 h/37° C./5% CO2. Then, cells are fixed with 4% Formaldehyde in PBS (15 min, RT). Following Nuclei are stained with Hoechst solution (3 μM PBS) and Cytoplasm with Cell Mask Blue (2 μg/ml PBS), 15 min, RT. Finally the stained cells are fixed with a second round of formaldehyde treatment. Fixed stained cells are washed and kept in PBS at 4° C. and can be read immediately until one month after preparation. That the binding of ApoA-I indeed reflected the level of ABCA1 in the cell, was demonstrated by loss of signal when ABCA1 expression was artificially reduced by transfection with small interfering RNA's.

The Alexa Fluor 647-labeled Apolipoprotein A-I (20 nM) was prepared as follows: Human recombinant Apolipoprotein A-I (ApoA-I) was exchanged to a buffer of 0.02 M $NaHCO_3$ at pH 8.2 on an NAP desalting column (GE Healthcare) and brought to a concentration to 40 μM (1.13 mg/ml) by adjustment with the same buffer. The ApoA-I was fluorescently labeled by incubation with Alexa Fluor carboxylic acid succimidyl ester (Alexa Fluor 647, Invitrogen A-20006) at a 2:1 molar ratio (Alexa to ApoA-I) for 1 h under shaking at RT. The remaining unconjugated label was removed by buffer exchange to 0.02M $NaHCO_3$ at pH 8.2.

Imaging and data collection were performed on an OPERA confocal microplate imaging reader using a 20× water immersion objective and UV360 or 405 laser to identify the cell nuclei and a 635 laser to identify the fluorescent ApoA-I. Eight fields of view are captured per well. Image capture and analysis was performed with the Acapella software. Background fluorescence detected in control wells without ApoA-I was subtracted.

Using XLfit3 program (ID Business Solutions Ltd. UK), the model 205 for Dose Response One Site is used to calculate the $EC_{50}$ values. The compounds of the present invention exhibit $EC_{50}$ values in a range of 0.1 μM to 10 μM in the ABCA1 protein detection assay. Particularly, the compounds of the present invention have $EC_{50}$ values in a range of 0.1 μM to 3 μM.

TABLE 1

ABCA1 protein increasing efficacy

| Example | % increase of ABCA1 at 3 μM |
|---|---|
| 1 | >45% @ 3 μM |
| 2 | >45% @ 3 μM |
| 3 | >45% @ 3 μM |
| 4 | >45% @ 3 μM |
| 5 | >45% @ 3 μM |
| 6 | >45% @ 3 μM |
| 7 | >45% @ 3 μM |
| 8 | >45% @ 3 μM |
| 9 | >45% @ 3 μM |
| 10 | >45% @ 3 μM |
| 11 | >45% @ 3 μM |
| 12 | >45% @ 3 μM |
| 13 | >45% @ 3 μM |

Cholesterol Efflux Assay

The ability of compounds of the invention to stimulate cholesterol efflux is determined in replicate cultures of THP-1 cells in 96-well microplates. Cells are plated at an initial density of 150,000 cells/well and differentiated to macrophages with the addition of PMA (100 ng/ml) for 72 hrs in 10% fetal bovine serum, 3 μl/L of b-mercaptoethanol, RPMI-1640 medium. Cells are washed once with RPMI-1640 and loaded with RPMI-1640 medium containing 2% FCS, 50 μg/ml acetylated LDL, and 10 μCi/ml [$^3$H]cholesterol for 48 hours at 37° C. After loading the cells are washed once with RPMI-1640 and incubated with the compound of interest from DMSO solutions for an additional 24 hrs in RPMI-1640 medium containing 1 mg/ml fatty acid free-bovine serum albumin (BSA). Upon incubation cells are washed once, and cholesterol efflux is induced by the addition of 10 μg/ml Apolipoprotein AI in RPMI-1640 containing 1 mg/ml BSA and in the presence of the compound for an additional 6 hrs. Following incubation radioactivity is determined in the supernatants and cholesterol efflux is expressed as the percent stimulation over replicate cultures treated only with DMSO. Sigmoidal curves were fitted using the XLfit3 program (ID Business Solutions Ltd. UK) and $EC_{50}$ values were determined.

The compounds of the present invention exhibit $EC_{50}$ values in a range of 0.1 μM to 3.0 μM in the cholesterol efflux assay. Particularly, the compounds of the present invention have $EC_{50}$ values in a range of 0.1 μM to 1.5 μM.

CB1 and CB2 Receptor Affinity

The affinity of the compounds of the invention for cannabinoid receptors was determined using membrane preparations of human embryonic kidney (HEK) cells in which the human CB1 receptor is transiently transfected using a Semliki Forest Virus system in conjunction with [3H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The affinity of the compounds of the invention for cannabinoid CB2 receptors was determined using membrane preparations of human embryonic kidney (HEK) cells in which the human CB2 receptor is transiently transfected using a Semliki Forest Virus system in conjunction with [$^3$H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The ability of the compounds to displace the radioligand [$^3$H]-CP-55,940 was measured at a concentration of 10 μM and values provided as [% inhibition @10 μM] both for the CB1 and CB2 receptor assay, The lower % inhibition is, the lower the likelihood of side effects based on CB1 or CB2 receptor inhibition is.

The compounds of the present invention exhibit values below 50% inhibition in both the CB1 and CB2 receptor assay at a concentration of 10 μM. In particular, the compounds of the present invention exhibit values below 35% inhibition in both the CB1 and CB2 receptor assays and even more particularly below 20% in both assays.

TABLE 2

CB1 and CB2-receptor affinity

| Example | CB1 receptor affinity [% inhibition @ 10 μM] | CB2 receptor affinity [% inhibition @ 10 μM] |
| --- | --- | --- |
| 1 | 4 | −9 |
| 2 | 22 | −12 |
| 3 | 26 | 0 |
| 4 | 34 | 2 |
| 5 | 28 | −8 |
| 6 | 40 | −5 |
| 7 | 21 | −12 |
| 8 | 28 | −13 |
| 9 | 27 | −9 |
| 10 | 13 | −8 |
| 11 | 33 | 3 |
| 12 | 19 | −13 |
| 13 | 38 | −13 |

Further demonstration of biological activities of the compounds of the present invention may be accomplished through the following in vivo assays that are well known in the art.

Effects on Plasma Lipid Levels in Lean, Chow Fed Rats

The effects of compounds of compounds of formula I on plasma lipid levels were determined in lean, chow-fed Sprague-Dawley rats with compounds administered by p.o. gavage. After one week of acclimatisation, blood samples were collected from 4 hour-fasted animals for plasma lipid determination. Animals were then assigned to treatment groups based on HDL-cholesterol levels. Compounds of formula I were administered by gavage, once daily for five days. Control animals received vehicle alone. Blood was collected on day five from 4 hour-fasted rats, 2 hours after a final treatment, for plasma lipid analysis. Total cholesterol, HDL-cholesterol, and triglycerides were determined by measuring total cholesterol, HDL-cholesterol, and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Obese, High Fat Diet Fed Rats

Efficacy of compounds in modulating plasma lipid levels was determined also in obese male Sprague Dawley rats after 28-29 days administration of compounds. Male Sprague—Dawley rats of 10 weeks of age were fed a high fat diet during 3 weeks. Obese rats were distributed in groups according to homogeneous BW and FI evaluated a week before the start of the treatment. Treatment was administered as food-Admix. On day 29, blood was taken in the morning under slight anesthesia (retro-orbital method) in post-prandial conditions i.e. 4 h after food was removed. Plasma was separated from blood by low speed centrifugation and selected organs were taken (e.g liver, fat). Total cholesterol, HDL-cholesterol, and triglycerides were determined by measuring total cholesterol, HDL-cholesterol, LDL-cholesterol and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol, LDL-cholesterol, and VLDL-cholesterol levels were also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Cholesterol/Fat Fed Hamsters

Efficacy of compounds in modulating plasma lipid levels was determined in hamsters after 5 days of daily administration of compounds. Male hamsters of 6-8 weeks of age were used in the studies. After one week of acclimatization, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol was also determined after selective precipitation of HDL from plasma by standard procedures.

Pharmaceutical Compositions

The compounds of formula I and/or their pharmaceutically acceptable salts can be used in the form of pharmaceutical compositions for enteral, parenteral or topical administration. They can be administered, for example, perorally, e.g. in the form of tablets, coated tablets, dragées, hard and soft gelatin capsules, solutions, emulsions or suspensions, orally, e.g. in the form of buccal cavities, rectally, e.g. in the form of suppositories, parenterally, e.g. in the form of injection solutions or infusion solutions for intramuscular, intravenous or subcutaneous injection, or topically, e.g. in the form of ointments, creams or oils. Oral administration is of particular interest.

The production of the pharmaceutical compositions can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The therapeutically effective amount or dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 100 mg, especially about 1 to 50 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 1-100 mg, particularly 5-50 mg, of a compound of formula I.

The following examples C1 to C3 illustrate typical compositions of the present invention, but serve merely as representative thereof.

Example C1

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example C2

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C3

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

EXAMPLES

MS=mass spectrometry; EI=electron ionization; ESI=electrospray; NMR data are reported in parts per million (δ) relative to internal tetramethylsilane and are referenced to the deuterium lock signal from the sample solvent ($d_6$-DMSO unless otherwise stated); coupling constants (J) are in Hertz, mp=melting point; bp=boiling point; HPLC=LC=high performance liquid chromatography, Rt=retention time, TLC=thin layer chromatography, HATU=2-(7-aza-1H-benzotriazole-1-yl)-1,1,3,3-tetramethyluronium hexafluorophosphate, TBTU=O-(benzotriazol-1-yl)-N,N,N',N'-tetramethyl-uronium-tetrafluoroborate; TEMPO=2,2,6,6-tetramethylpiperidine 1-oxyl radical, DMF=dimethylformamide, DIPEA=N,N-diisopropylethylamine, DMSO=dimethyl-sulfoxide, THF=tetrahydrofuran, CAN=CAS Registry Number.

Example 1

Preparation of N-[5-cyclopentyl-6-(2,2,2-trifluoro-ethoxy)-pyridin-3-yl]-5-methoxy-nicotinamide a) 3-Bromo-5-nitro-2-(2,2,2-trifluoro-ethoxy)-pyridine

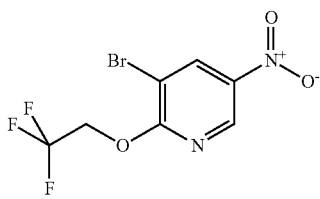 [SMILES: O=[N+]([O-])c1cnc(OCC(F)(F)F)c(Br)c1]

To 1,1,1-trifluoroethanol (180 mL) was added sodium hydride (60% in oil, 10 g, 252.7 mmol) in portions at 0-5° C. and the reaction mixture was stirred at 25° C. for 30 min. To this solution was added 3-bromo-2-chloro-5-nitro-pyridine (CAN 5470-17-7) (6 g, 25.3 mmol) in trifluoroethanol (20 mL) drop wise and the reaction mixture was refluxed for 12 h. The solvent was removed in vacuo, and the residue was taken up in water and extracted with ethyl acetate (3×200 mL). Combined organic layers were washed with water (200 mL), brine, dried with $Na_2SO_4$ and concentrated. The crude material was purified by column chromatography (Combi-Flash, 40 g, 5% dichloromethane/hexane) to get the title compound (5.7 g, 74.9%) as white solid; NMR complies.

b) 3-Cyclopent-1-enyl-5-nitro-2-(2,2,2-trifluoro-ethoxy)-pyridine

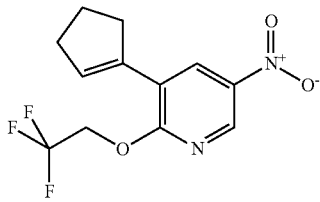 [SMILES: O=[N+]([O-])c1cnc(OCC(F)(F)F)c(C2=CCCC2)c1]

To a stirred solution of 3-bromo-5-nitro-2-(2,2,2-trifluoro-ethoxy)-pyridine (Example 1a) (6 g, 19.9 mmol) in DMF (30 mL) was added 2-(1-cyclopenten-1-yl)-4,4,5,5-tetramethyl-1,3,2-dioxaborolane (CAN 287944-10-9) (4.64 g, 23.9 mmol) and $K_2CO_3$ (8.2 g, 59.8 mmol) at 25° C. and the reaction mixture was degassed with argon over 30 min. To this was added $PdCl_2$ $(dppf)_2$ dichloromethane complex (814 mg, 1.1 mmol) and the reaction mixture was heated to 80° C. for 20 h. The reaction mixture cooled to 25° C., water (50 mL) was added, the mixture was extracted with ethyl acetate (4×50 mL), washed with water (200 mL), brine, dried with $Na_2SO_4$ and concentrated. The crude material was purified by column chromatography (Combi-Flash, 40 g, 2% dichloromethane/hexane) to get the title compound (2.5 g, 43.51%) as pale white solid; NMR complies.

c) 5-Cyclopentyl-6-(2,2,2-trifluoro-ethoxy)-pyridin-3-ylamin

To a solution of 3-cyclopent-1-enyl-5-nitro-2-(2,2,2-trifluoro-ethoxy)-pyridine (Example 1b) (600 mg, 2.08 mmol) in ethyl acetate (30 mL) was added 10% Pd/C (554 mg, 0.52 mmol) under argon atmosphere. The reaction mixture was stirred under hydrogen balloon pressure for 12 h. The catalyst was filtered off and the filtrate was concentrated under reduced pressure. The crude thus obtained was purified by column chromatography (Combi-Flash, 40 g, 25% ethyl acetate/hexane) to get the title compound (375 mg, 69.16%) as colorless liquid; MS (ESI): 259 [M−H]⁻.

d) N-[5-Cyclopentyl-6-(2,2,2-trifluoro-ethoxy)-pyridin-3-yl]-5-methoxy-nicotinamide

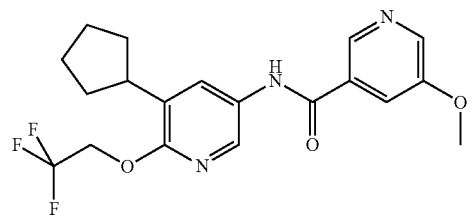 [SMILES: COc1cncc(C(=O)Nc2cnc(OCC(F)(F)F)c(C3CCCC3)c2)c1]

This compound was prepared following the same procedure as described for Example 3 using 5-cyclopentyl-6-(2,2,2-trifluoro-ethoxy)-pyridin-3-ylamine (Example 1c) (100 mg, 0.33 mmol) and 5-methoxy-nicotinic acid (50.49 mg, 0.33 mmol) as starting materials. The title compound (73 mg, 48.2%) was isolated as off white solid; MS (ESI): 396 [M+H]⁺.

Example 2

Preparation of 5-methyl-2H-pyrazole-3-carboxylic acid [5-cyclopentyl-6-(2,2,2-trifluoro-ethoxy)-pyridin-3-yl]-amide

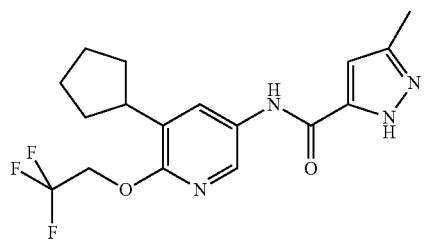 [SMILES: Cc1cc(C(=O)Nc2cnc(OCC(F)(F)F)c(C3CCCC3)c2)[nH]n1]

This compound was prepared following the same procedure as described for Example 3 using 5-cyclopentyl-6-(2,2,2-trifluoro-ethoxy)-pyridin-3-ylamine (Example 1c) (100 mg, 0.33 mmol) and 5-methyl-2H-pyrazole-3-carboxylic acid (41.6 mg, 0.33 mmol) as starting materials. The title compound (33 mg, 23.4%) was isolated as off white solid; MS (ESI): 369 [M+H]+.

Example 3

Preparation of 5-methyl-oxazole-4-carboxylic acid [5-cyclopentyl-6-(2,2,2-trifluoro-ethoxy)-pyridin-3-yl]-amide

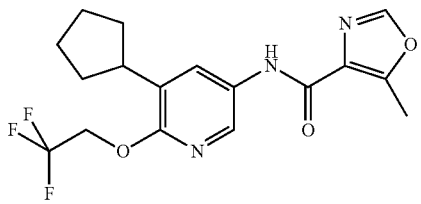 [SMILES: Cc1ocnc1C(=O)Nc1cnc(OCC(F)(F)F)c(C2CCCC2)c1]

To a solution of 5-methyl-4-oxazolecarboxylic acid (CAN 103879-58-9) (73 mg, 0.57 mmol) in DMF (4 mL) were added DIPEA (0.1 mL, 1.15 mmol) and HATU (219 mg, 0.57 mmol) at 25° C. The reaction mixture was stirred for 30 min at 25° C. Then, 5-cyclopentyl-6-(2,2,2-trifluoro-ethoxy)-pyridin-3-ylamine (Example 1c) (100 mg, 0.38 mmol) was added and the reaction mixture was stirred at 25° C. for 12 h. Volatiles were removed in vacuo and the resultant residue was purified by prep-HPLC to get the title compound (30 mg, 21.3%) as off-white solid. MS (ESI): 370 [M+H]+.

Example 4

Preparation of N-[5-cyclopentyl-6-(2,2,2-trifluoro-ethoxy)-pyridin-3-yl]-nicotinamide

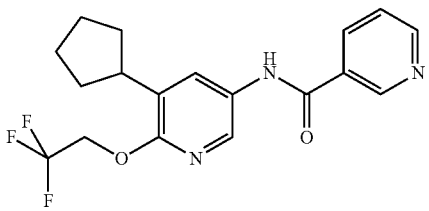 [SMILES: O=C(Nc1cnc(OCC(F)(F)F)c(C2CCCC2)c1)c1cccnc1]

This compound was prepared following the same procedure as described for Example 3 using 5-cyclopentyl-6-(2,2,2-trifluoro-ethoxy)-pyridin-3-ylamine (Example 1c) (100 mg, 0.38 mmol) and nicotinic acid (40.6 mg, 0.33 mmol) as starting materials. The title compound (61 mg, 43.3%) was isolated as off white solid; MS (ESI): 366 [M+H]+.

Example 5

Preparation of pyridine-2-carboxylic acid [5-cyclopentyl-6-(2,2,2-trifluoro-ethoxy)-pyridin-3-yl]-amide

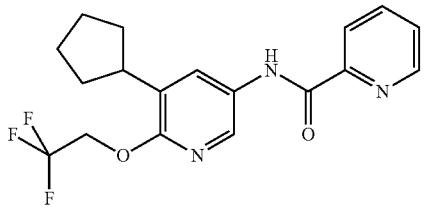 [SMILES: O=C(Nc1cnc(OCC(F)(F)F)c(C2CCCC2)c1)c1ccccn1]

This compound was prepared following the same procedure as described for Example 3 using 5-cyclopentyl-6-(2,2,2-trifluoro-ethoxy)-pyridin-3-ylamine (Example 1c) (100 mg, 0.38 mmol) and pyridine-2-carboxylic acid (41 mg, 0.33 mmol) as starting materials. The title compound (66 mg, 46.8%) was isolated as off white solid; MS (ESI): 366 [M+H]+.

Example 6

Preparation of N-[5-cyclopentyl-6-(2,2,2-trifluoro-ethoxy)-pyridin-3-yl]-benzamide

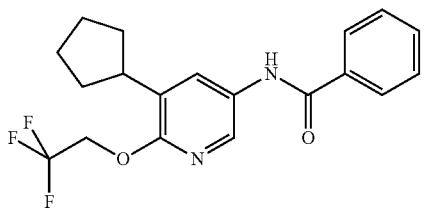 [SMILES: O=C(Nc1cnc(OCC(F)(F)F)c(C2CCCC2)c1)c1ccccc1]

This compound was prepared following the same procedure as described for Example 3 using 5-cyclopentyl-6-(2,2,2-trifluoro-ethoxy)-pyridin-3-ylamine (Example 1c) (100 mg, 0.38 mmol) and benzoic acid (40 mg, 0.33 mmol) as starting materials. The title compound (69 mg, 49.3%) was isolated as off white solid; MS (ESI): 365 [M+H]+.

Example 7

Preparation of pyrimidine-5-carboxylic acid [5-cyclopentyl-6-(2,2,2-trifluoro-ethoxy)-pyridin-3-yl]-amide

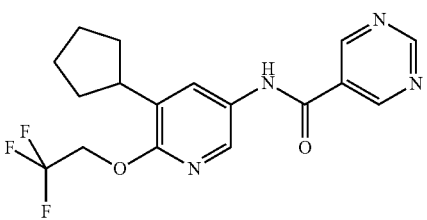 [SMILES: O=C(Nc1cnc(OCC(F)(F)F)c(C2CCCC2)c1)c1cncnc1]

This compound was prepared following the same procedure as described for Example 3 using 5-cyclopentyl-6-(2,2,2-trifluoro-ethoxy)-pyridin-3-ylamine (Example 1c) (100 mg, 0.38 mmol) and pyrimidine-5-carboxylic acid (41 mg, 0.33 mmol) as starting materials. The title compound (23 mg, 15.7%) was isolated as off white solid; MS (ESI): 367 [M+H]$^+$.

Example 8

Preparation of N-[5-cyclohexyl-6-(2,2,2-trifluoro-ethoxy)-pyridin-3-yl]-nicotinamide a) 3-Cyclohex-1-enyl-5-nitro-2-(2,2,2-trifluoro-ethoxy)-pyridine

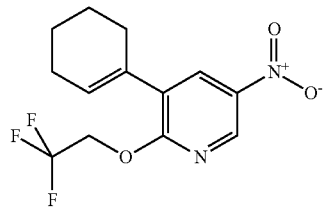 [SMILES: O=[N+]([O-])c1cnc(OCC(F)(F)F)c(C2=CCCCC2)c1]

This compound was prepared following the same procedure as described for Example 1b using 3-bromo-5-nitro-2-(2,2,2-trifluoro-ethoxy)-pyridine (Example 1a, 1 g, 3.18 mmol) and 2-(1-cyclohexen-1-yl)-4,4,5,5-tetramethyl-1,3,2-dioxaborolane (CAN 141091-37-4, 0.73 g, 3.5 mmol) as starting materials. The title compound (520 mg, 54.0%) was isolated as off white solid; NMR complies.

b) 5-Cyclohexyl-6-(2,2,2-trifluoro-ethoxy)-pyridin-3-ylamine

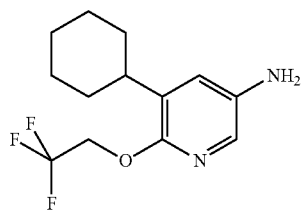 [SMILES: Nc1cnc(OCC(F)(F)F)c(C2CCCCC2)c1]

This compound was prepared following the same procedure as described for Example 1c using 3-cyclohex-1-enyl-5-nitro-2-(2,2,2-trifluoro-ethoxy)-pyridine (Example 8a, 500 mg, 1.66 mmol) as starting material. The title compound (300 mg, 66.1%) was isolated as off white solid; MS (ESI): 275.4 [M+H]$^+$.

c) N-[5-cyclohexyl-6-(2,2,2-trifluoro-ethoxy)-pyridin-3-yl]-nicotinamide

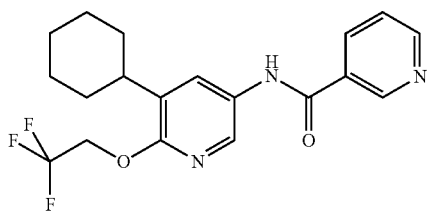 [SMILES: O=C(Nc1cnc(OCC(F)(F)F)c(C2CCCCC2)c1)c1cccnc1]

This compound was prepared following the same procedure as described for Example 3 using 5-cyclohexyl-6-(2,2,2-trifluoro-ethoxy)-pyridin-3-ylamine (Example 8b) (100 mg, 0.36 mmol) and nicotinic acid (40.6 mg, 0.33 mmol) as starting materials. The title compound (54 mg, 39.9%) was isolated as off white solid; MS (ESI): 380 [M+H]$^+$.

Example 9

Preparation of 5-methyl-2H-pyrazole-3-carboxylic acid [5-cyclohexyl-6-(2,2,2-trifluoro-ethoxy)-pyridin-3-yl]-amide

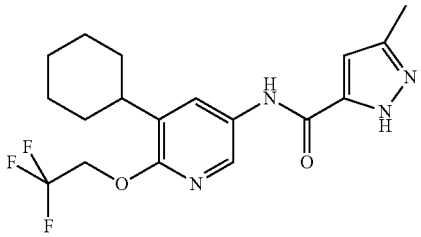 [SMILES: Cc1cc(C(=O)Nc2cnc(OCC(F)(F)F)c(C3CCCCC3)c2)[nH]n1]

This compound was prepared following the same procedure as described for Example 3 using 5-cyclohexyl-6-(2,2,2-trifluoro-ethoxy)-pyridin-3-ylamine (Example 8b) (100 mg, 0.36 mmol) and 5-methyl-2H-pyrazole-3-carboxylic acid (40.6 mg, 0.33 mmol) as starting materials. The title compound (67 mg, 48.2%) was isolated as off white solid; MS (ESI): 383 [M+H]$^+$.

Example 10

Preparation of 5-methyl-oxazole-4-carboxylic acid [5-cyclohexyl-6-(2,2,2-trifluoro-ethoxy)-pyridin-3-yl]-amide

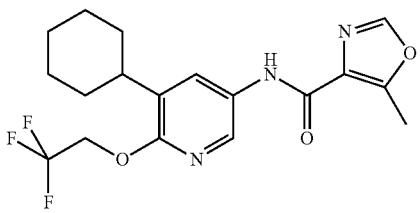 [SMILES: Cc1ocnc1C(=O)Nc1cnc(OCC(F)(F)F)c(C2CCCCC2)c1]

This compound was prepared following the same procedure as described for Example 3 using 5-cyclohexyl-6-(2,2,2-trifluoro-ethoxy)-pyridin-3-ylamine (Example 8b) (100 mg, 0.36 mmol) and 5-methyl-4-oxazolecarboxylic acid (71 mg, 0.55 mmol) as starting materials. The title compound (67 mg, 47.2%) was isolated as off white solid; MS (ESI): 384 [M+H]$^+$.

Example 11

Preparation of pyridine-2-carboxylic acid [5-cyclohexyl-6-(2,2,2-trifluoro-ethoxy)-pyridin-3-yl]-amide

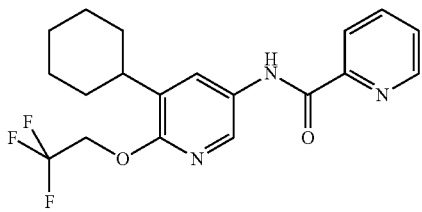 [SMILES: O=C(Nc1cnc(OCC(F)(F)F)c(C2CCCCC2)c1)c1ccccn1]

This compound was prepared following the same procedure as described for Example 3 using 5-cyclohexyl-6-(2,2,2-trifluoro-ethoxy)-pyridin-3-ylamine (Example 8b) (100 mg, 0.36 mmol) and pyridine-2-carboxylic acid (41 mg, 0.33 mmol) as starting materials. The title compound (50 mg, 36.2%) was isolated as off white solid; MS (ESI): 380 [M+H]$^+$.

Example 12

Preparation of N-[5-cyclohexyl-6-(2,2,2-trifluoro-ethoxy)-pyridin-3-yl]-5-methoxy-nicotinamide

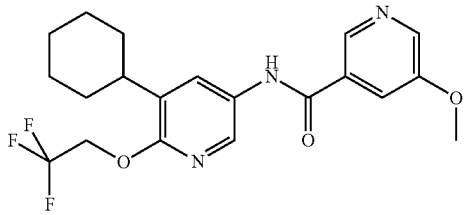 [SMILES: COc1cncc(C(=O)Nc2cnc(OCC(F)(F)F)c(C3CCCCC3)c2)c1]

This compound was prepared following the same procedure as described for Example 3 using 5-cyclohexyl-6-(2,2,2-trifluoro-ethoxy)-pyridin-3-ylamine (Example 8b) (100 mg, 0.36 mmol) and 5-methoxy-nicotinic acid (50.5 mg, 0.33 mmol) as starting materials. The title compound (76 mg, 51.0%) was isolated as off white solid; MS (ESI): 410 [M+H]$^+$.

Example 13

Preparation of N-[5-cyclohexyl-6-(2,2,2-trifluoro-ethoxy)-pyridin-3-yl]-benzamide

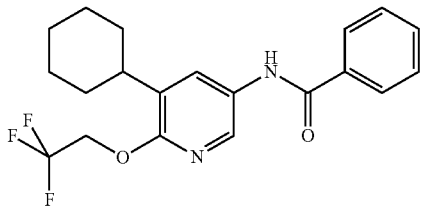 [SMILES: O=C(Nc1cnc(OCC(F)(F)F)c(C2CCCCC2)c1)c1ccccc1]

This compound was prepared following the same procedure as described for Example 3 using 5-cyclohexyl-6-(2,2,2-trifluoro-ethoxy)-pyridin-3-ylamine (Example 8b) (100 mg, 0.36 mmol) and benzoic acid (40 mg, 0.33 mmol) as starting materials. The title compound (60 mg, 43.5%) was isolated as off white solid; MS (ESI): 379 [M+H]$^+$.

The invention claimed is:

1. A compound according to formula (I),

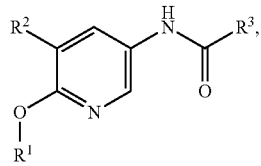

wherein

R$^1$ is selected from the group consisting of C$_{1-7}$-alkyl,
C$_{3-7}$-cycloalkyl,
C$_{3-7}$-cycloalkyl-C$_{1-7}$-alkyl,
hydroxy-C$_{1-7}$-alkyl,
C$_{1-7}$-alkoxy-C$_{1-7}$-alkyl, and
halogen-C$_{1-7}$-alkyl;

R$^2$ is selected from the group consisting of
C$_{3-7}$-cycloalkyl,
C$_{4-7}$-cycloalkenyl; and R$^3$ is selected from the group consisting of
phenyl, wherein phenyl is unsubstituted or substituted by one or two groups selected from the group consisting of C$_{1-7}$-alkyl, hydroxy, C$_{1-7}$-alkoxy, cyano, C$_{3-7}$-cycloalkyl, C$_{3-7}$-cycloalkyl-C$_{1-7}$-alkyl, halogen and halogen-C$_{1-7}$-alkyl, and
heteroaryl, wherein heteroaryl is unsubstituted or substituted by one or two groups selected from the group consisting of C$_{1-7}$-alkyl, hydroxy, C$_{1-7}$-alkoxy, cyano, C$_{3-7}$-cycloalkyl, C$_{3-7}$-cycloalkyl-C$_{1-7}$-alkyl, halogen and halogen-C$_{1-7}$-alkyl;

or a pharmaceutically acceptable salt thereof.

2. A compound according to claim 1, wherein R$^1$ is halogen-C$_{1-7}$-alkyl.

3. A compound according to claim 1, wherein R$^2$ is C$_{3-7}$-cycloalkyl or C$_{4-7}$-cycloalkenyl.

4. A compound according to claim 1, wherein R$^2$ is cyclopentyl or cyclohexyl.

5. A compound according to claim 1, wherein R$^3$ is
phenyl, wherein phenyl is unsubstituted or substituted by one or two groups selected from the group consisting of C$_{1-7}$-alkyl, hydroxy, C$_{1-7}$-alkoxy, cyano, C$_{3-7}$-cycloalkyl, C$_{3-7}$-cycloalkyl-C$_{1-7}$-alkyl, halogen and halogen-C$_{1-7}$-alkyl.

6. A compound according to claim 1, wherein R$^3$ is
heteroaryl, wherein heteroaryl is unsubstituted or substituted by one or two groups selected from the group consisting of C$_{1-7}$-alkyl, hydroxy, C$_{1-7}$-alkoxy, cyano, C$_{3-7}$-cycloalkyl, C$_{3-7}$-cycloalkyl-C$_{1-7}$-alkyl, halogen and halogen-C$_{1-7}$-alkyl.

7. A compound according to claim 1, wherein R$^3$ is
heteroaryl, said heteroaryl being selected from the group consisting of furanyl, oxazolyl, isoxazolyl, pyrazolyl, oxadiazolyl, thiazolyl, isothiazolyl, thiodiazolyl, pyridyl, pyridazinyl, pyrimidinyl and pyrazinyl, and being unsubstituted or substituted by one or two groups selected from the group consisting of C$_{1-7}$-alkyl, hydroxy, C$_{1-7}$-alkoxy, cyano, C$_{3-7}$-cycloalkyl, C$_{3-7}$-cycloalkyl-C$_{1-7}$-alkyl, halogen and halogen-C$_{1-7}$-alkyl.

8. A compound according to claim 1, wherein $R^3$ is selected from the group consisting of phenyl, 5-methyl-oxazol-4-yl, 5-methyl-2H-pyrazol-3-yl, pyridin-2-yl, pyridin-3-yl, 5-methoxy-pyridin-3-yl and pyrimidin-5-yl.

9. A compound according to claim 1, selected from the group consisting of N-[5-cyclopentyl-6-(2,2,2-trifluoro-ethoxy)-pyridin-3-yl]-5-methoxy-nicotinamide, 5-methyl-2H-pyrazole-3-carboxylic acid [5-cyclopentyl-6-(2,2,2-trifluoro-ethoxy)-pyridin-3-yl]-amide, 5-methyl-oxazole-4-carboxylic acid [5-cyclopentyl-6-(2,2,2-trifluoro-ethoxy)-pyridin-3-yl]-amide, N-[5-cyclopentyl-6-(2,2,2-trifluoro-ethoxy)-pyridin-3-yl]-nicotinamide, pyridine-2-carboxylic acid [5-cyclopentyl-6-(2,2,2-trifluoro-ethoxy)-pyridin-3-yl]-amide, N-[5-cyclopentyl-6-(2,2,2-trifluoro-ethoxy)-pyridin-3-yl]-benzamide, pyrimidine-5-carboxylic acid [5-cyclopentyl-6-(2,2,2-trifluoro-ethoxy)-pyridin-3-yl]-amide, N-[5-cyclohexyl-6-(2,2,2-trifluoro-ethoxy)-pyridin-3-yl]-nicotinamide, 5-methyl-2H-pyrazole-3-carboxylic acid [5-cyclohexyl-6-(2,2,2-trifluoro-ethoxy)-pyridin-3-yl]-amide, 5-methyl-oxazole-4-carboxylic acid [5-cyclohexyl-6-(2,2,2-trifluoro-ethoxy)-pyridin-3-yl]-amide, pyridine-2-carboxylic acid [5-cyclohexyl-6-(2,2,2-trifluoro-ethoxy)-pyridin-3-yl]-amide, N-[5-cyclohexyl-6-(2,2,2-trifluoro-ethoxy)-pyridin-3-yl]-5-methoxy-nicotinamide, N-[5-cyclohexyl-6-(2,2,2-trifluoro-ethoxy)-pyridin-3-yl]-benzamide, and pharmaceutically acceptable salts thereof.

10. A compound according to claim 1, selected from the group consisting of pyrimidine-5-carboxylic acid [5-cyclopentyl-6-(2,2,2-trifluoro-ethoxy)-pyridin-3-yl]-amide, pyridine-2-carboxylic acid [5-cyclohexyl-6-(2,2,2-trifluoro-ethoxy)-pyridin-3-yl]-amide, N-[5-cyclohexyl-6-(2,2,2-trifluoro-ethoxy)-pyridin-3-yl]-5-methoxy-nicotinamide, and pharmaceutically acceptable salts thereof.

11. A pharmaceutical composition comprising a compound according to claim 1 and a pharmaceutically acceptable carrier and/or adjuvant.

\* \* \* \* \*